United States Patent [19]

Stephan

[11] Patent Number: 5,726,335
[45] Date of Patent: Mar. 10, 1998

[54] ZIRCONIUM COMPOUNDS, THEIR PREPARATION AND THEIR USE AS CATALYSTS

[75] Inventor: Douglas W. Stephan, La Salle, Canada

[73] Assignee: University of Windsor, Ontario, Canada

[21] Appl. No.: 571,294

[22] Filed: Dec. 12, 1995

[51] Int. Cl.$^6$ .............................. C07F 17/00; B01J 31/00
[52] U.S. Cl. .............................. 556/53; 502/152
[58] Field of Search .............................. 556/53

[56] References Cited

U.S. PATENT DOCUMENTS

| | | | |
|---|---|---|---|
| 4,147,709 | 4/1979 | Lynch | 556/53 |
| 4,366,101 | 12/1982 | Gibson | 556/53 |

OTHER PUBLICATIONS

Y. Yamaguchi, "Catalytic Oligomerization of Primary Phosphines by an Anionic Zirconium Hydride Complex", Organomet. News, No. 4, p. 129.

K.I. Gell, J. Schwartz, "Hydrogenation of d$^0$ Complexes: Zirconium (IV) Alkyl Hydrides", Journal of the American Chemical Society, 100, 3246 (1978).

P.T. Wolczanski, J.E. Bercaw, "Dihydrogen Reduction of Isocyanides Promoted by Permethylzirconocene Dihydride. A Modeling Study of Carbon Monoxide Reduction", Journal of the American Chemical Society, 101, 6450 (1979).

P.T. Wolczanski, R.S. Threlkel, J.E. Bercaw, "Reduction of Coordinated Carbon Monoxide to Zirconoxy Carbenes with Permethylzirconocene Dihydride", Journal of the American Chemical Society, 101, 218 (1979).

D.R. McAlister, D.K. Erwin, J.E. Bercaw, "Reductive Elimination of Isobutane from an Isobutyl Hydride Derivative of Bis(pentamethylcyclopentadienyl)zirconium", Journal of the American Chemical Society, 100, 5966 (1978).

J.M. Manriquez, D.R. McAlister, R.D. Sanner, J.E. Bercaw, "Stoichiometric Hydrogen Reduction of Carbon Monoxide to Methanol Promoted by Derivatives of Bis(pentamethylcyclopentadienyl)zirconium", Journal of the American Chemical Society, 98, 6733 (1976).

J.M. Manriquez, D.R. McAlister, R.D. Sanner, J.E. Bercaw, "Reduction of Carbon Monoxide Promoted by Alkyl and Hydride Derivatives of Permethylzirconocene", Journal of the American Chemical Society, 100, 2716 (1978).

M. Fermin et al., J. Am. Chem. Soc., vol. 117, pp. 12645–12646, Dec. 1995.

N. Etkin et al., J. Am. Chem. Soc., vol. 119, pp. 2954–2955, Mar. 1997.

Primary Examiner—Glenn Caldarola
Assistant Examiner—J. Pasterczyk
Attorney, Agent, or Firm—Ratner & Prestia

[57] ABSTRACT

Novel mononuclear $Z^{IV}$ trihydride, monoalkyl dihydride and deuteride compounds are prepared and are used as catalysts in dehydrocoupling reactions.

14 Claims, No Drawings

ZIRCONIUM COMPOUNDS, THEIR PREPARATION AND THEIR USE AS CATALYSTS

The present invention relates to a class of novel zirconium-containing compounds and their utility as catalysts.

In one aspect the invention provides novel $Zr^{IV}$ compounds of general formula I

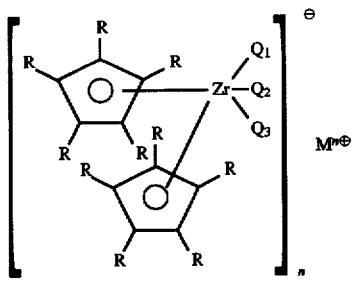

wherein R is H or an electron-donating group, provided that at least two R groups, preferably at least three R groups, attached to each cyclopentadienyl ring are other than H, M is a counter ion, $Q_1$ is H, D or $CH_3$, $Q_2$ and $Q_3$ are H or D, and n is the valency of the counter ion, or a solvate thereof.

Thus the novel compounds contain a mononuclear $Zr^{IV}$ trihydride or deuteride anion and the cation M, end the hydride can bear hydrogen or deuterium atoms, as shown. It is possible that one of the hydrogen or deuterium atoms of the anion is replaced by a small alkyl group, e.g., methyl, as shown.

The group R is an electron-donating group and suitable examples of such groups include alkyl and alkenyl group preferably containing up to about 8 carbon atoms in the alkyl or alkenyl chain. The alkyl or alkenyl groups can be substituted, provided that the substituents do not have the effect of rendering the group non-electron-donating and also provided that the substituents do not interfere with the zirconium centre. Suitable substituents include fluorine atoms and alkoxy, e.g. methoxy or ethoxy, cycloalkyl, e.g., cyclopentyl or cyclohexyl, phenyl and ester functions, e.g. lower alkoxycarbonyl functions such as acetoxy and proplonyloxy. The phenyl or cyclohexyl substituents can, in turn, be further substituted by alkyl, fluorine, alkoxy, phenyl, cycloalkyl or ester functions. In these R groups one or more carbon atoms can be replaced by silicon atoms. As examples of silicon-containing R groups there are mentioned the trimethylsilyl and trimethylsilylmethyl groups.

Preferred counter ions M include monovalent-$Na^+$, $K^+$, $Li^+$ and tetraalkylammonium ions and the divalent ions $Ca^{2+}$ and $Mg^{2+}$. The tetraalkylammonium ions can have up to about 8 carbon atoms per alkyl group; mention is made particularly of tetraethyl and tetra-n-butyl ammonium ions.

The compounds of formula I can be obtained by reacting a compound of the general formula II

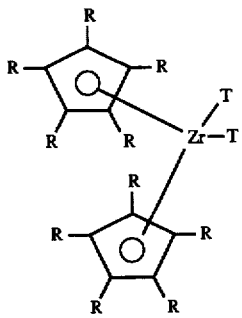

wherein R is as defined above and T is a suitable leaving group, for example a halogen atom, with an effective hydrogen transfer reagent.

Alternatively, the required trihydride can be made from the corresponding dihydride of formula

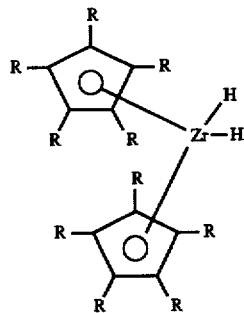

This can be done by reaction with the hydrogen transfer reagent. The dihydride can be obtained by reacting a compound of the general formula II, preferably the chloride, with magnesium in tetrahydrofuran (THF) under nitrogen. This yields the known species $[Cp_2^*ZrN_2]_2$ [μ-N2], which can be converted readily to the dihydride by treatment with hydrogen, for example at 0° C. in toluene or hexane.

To prepare a compound of the general formula I in which a methyl group is present the corresponding trihydride can be prepared and then reacted with methyl lithium or a Grignard reagent.

In general, effective hydrogen transfer agents are known to persons skilled in the art, and suitable hydrogen transfer reagents include potassium hydride, sodium hydride, lithium hydride, substituted aluminum hydrides such as $LiAlH_4$, $NaAlH_4$, LiAl H(alkoxide)$_3$ for example LiAlH(tert-butoxide)$_3$, sodium borohydride, calcium hydride and magnesium hydride. To obtain compounds of formula I containing deuterium in place of hydrogen there can be used a deuterium transfer agent, i.e., a transfer agent containing deuterium in place of hydrogen.

The trihydride compound of formula I can bear hydrogen atoms or deuterium atoms. It should be appreciated that in the following description references to "hydrogen" or "hydride" apply also to "deuterium" and "deuteride", unless the context indicates otherwise.

The counter ion M will normally be derived from the hydrogen transfer reagent that is reacted with the compound of formula II. Thus, if the reagent is potassium hydride, lithium aluminum hydride or sodium borohydride the counter ion will be potassium, lithium or sodium, respectively. To obtain a compound in which M is a tetraalkylammonium ion there can be used a tetraalkyl ammonium borohydride, for example tetraethylammonium borohydride, as hydrogen transfer reagent. It is possible to subject an obtained compound of formula I to an ion exchange reaction to change one value of counter ion M to another value. For example, a potassium counter ion can be replaced by a tetraalkylammonium ion by cationic exchange with tetraalkylammonium salts, especially halides, suitably in an ether as solvent. Purification by recrystallization may be required.

In the compound of formula II, the leaving group T can be fluorine, chlorine, bromine or iodine but, in the preferred embodiment, T is chlorine. In a particularly preferred embodiment the compound of formula II is di- pentamethylcyclopentadienylzirconium dichloride, which is commercially available from Aldrich Chemical Company.

The reaction of the compound of formula II with the hydrogen transfer agent is carried out in a suitable organic solvent. Ethers are suitable solvents, as the product of formula I is soluble in ethers. The counter ion may form a complex with the ether solvent. As examples of suitable ethers there are mentioned particularly tetrahydrofuran (THF), dimethyl ether and dioxane.

The reaction will take place at room temperature over several hours. The excess hydrogen transfer reagent is then removed from the reaction mixture, suitably by filtration and if required the compound of formula I can be separated from the reaction mixture. The compound can be precipitated by, for example, addition of an inert hydrocarbon solvent, or cooling, or both. As suitable inert hydrocarbon solvents are mentioned pentane, hexane, benzene, toluene, xylene and the like.

As stated, the hydrogen transfer reagent is present in excess When reacted with the compound of formula II; in the absence of excess hydrogen transfer reagent the required mononuclear $Zr^{IV}$ trihydride anion may not be formed. Desirably two or more equivalents of hydrogen transfer reagent are used per equivalent of formula II, more preferably four or five equivalents. There is no particular upper limit on the excess, but nor is there any particular advantage in exceeding about a fourfold or fivefold excess.

The product of formula I may be sensitive to moisture or oxygen and should therefore be handled with appropriate precautions, for instance under nitrogen or argon in a dry box or using Schlenk line techniques.

It is within the scope of the present invention to include a cationic chelating reagent, for example a crown ether, in the reaction mixture, or in a solution of the purified product of formula I. This will sequester the counter ion, hence enhancing catalytic reactivity of the trihydride anion and possibly also enhancing solubility in non-polar solvents. The particular crown ether will depend upon the particular counter ion. For Instance lithium can be chelated with 12-crown-4. For alkali metals in general 18-crown-6 is of value.

As indicated above, the cyclopentadienyl moieties of the compound of formula I must be substituted. Unless the cyclopentadienyl moieties of the compound of formula II bear electron donating groups the reaction with the hydrogen transfer reagent does not result in the required trihydride anion; instead the reaction results in a dihydride compound. For instance, reaction of dicyclopentadienyl zirconium dichloride, i.e., the compound of formula II in which all R groups are hydrogen, with a hydrogen transfer reagent yields a dihydride, not the required $Zr^{IV}$ trihydride anion, as does reaction of di-(trimethylsilylcyclopentadienyl) zirconium dichloride. A preferred compound of formula II contains pentamethyl substituted cyclopentadienyl moieties; as mentioned above the dichloride of this compound is commercially available from Aldrich. Another preferred compound is di- (pentaethylcyclopentadienyl)zirconium dichloride, i.e., the compound in which all R groups are ethyl groups. The R groups are preferably alkyl groups containing up to about 8 carbon atoms, although as the number of carbon atoms increases the propensity of the compounds to crystallize is reduced and hence they are less readily handled. It should be appreciated that all R groups need not be identical, i.e., it is possible for one cyclopentadienyl moiety to be substituted by different alkyl groups and for the two cyclopentadienyl moieties to have different substituents. It is desirable that the substituents on the cyclopentadienyl moieties are sufficiently large to prevent dimerization of the reaction product.

The $Zr^{IV}$ trihydride compounds of formula I differ markedly in properties from the related dihydride compounds. The trihydride compounds of formula I are very good hydride donors, and in the compounds of formula I the usual Lewis acid behaviour of zirconium compounds is suppressed. The $Zr^{IV}$ trihydride compounds are effective catalysts in reactions in which hydrogen atoms are abstracted from molecules and the molecules are then coupled. As demonstrated below, potassium di(pentamethylcyclopentadienyl)zirconium trihydride catalyzes oligomerization of phosphorus compounds, silicon compounds and carbon compounds.

In another aspect, therefore, the invention provides a process in which a compound of formula I catalyzes coupling, for example oligomerization or polymerization, of a monomer bearing terminal hydrogen atoms. As examples of monomers that can be oligomerized are mentioned phosphorus containing compounds such as phosphines, hydrocarbon compounds and silicon-containing compounds such as silanes. The coupling reaction can be carried out in a solvent and preferred solvents include ethers, such as the ethers used as solvent in the reaction to form the compound of formula I, and inert hydrocarbons, especially aromatic hydrocarbons such as benzene, toluene and xylene. Heat can be applied if required.

It is possible to carry out the coupling reaction using a compound of formula I that is prepared in situ. Thus, the compound of formula II is reacted with the hydrogen transfer reagent and the monomer to be coupled is also present in the reaction mixture. As the $Zr^{IV}$ anion is formed it catalyzes the coupling reaction.

Care may be required to avoid interference between excess hydrogen transfer reagent and the substrate subjected to dehydrocoupling. No problem is encountered if the substrate Is a hydrocarbon. If the substrate is a phosphine a sacrificial amount of phosphine can be added to consume the excess hydrogen transfer reagent. Alternatively, the trihydride compound of formula I can be prepared from the corresponding dihydride, as described above. As two of the required hydrogen atoms are already in place, only one equivalent of hydrogen transfer reagent is required, so the in situ reaction can be carried out without large excess of hydrogen transfer reagent.

The coupling is described particularly with reference to the oligomerization of phenylphosphine by the catalytic effect of potassium di-(pentamethylcyclo pentadienyl) zirconium trihydride. In the formulae the symbol "Cp*" is used to indicate the pentamethylcyclo-pentadienyl moiety. The reaction proceeds as follows:

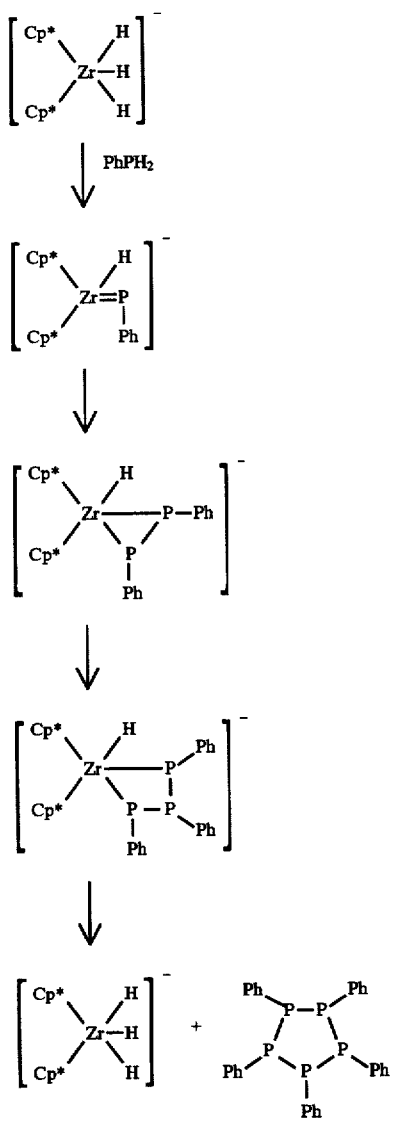

This reaction proceeds to the formation of intermediate (d) at room temperature but heat, say to about 60° C. to 80° C. or more, is required for conversion of intermediate (d) into pentaphenylcyclopentaphosphane. The intermediates (c) and (d) have been isolated and characterized by means of NMR spectra, elemental analysis and preliminary X-ray crystallographic data for (c). This oligomerization reaction to form a five-membered ring oligomer has been carried out with phenyl phosphine and also with cyclohexylphosphine and with 2,4,6-trimethyl-phenyl phosphine, with formation of the corresponding penta-substituted cyclopentaphosphane.

As the catalytic reaction involves abstraction of a hydrogen atom it is necessary that the monomer to undergo coupling bears one or more hydrogen atoms. If the monomer bears one hydrogen atom there will be formed a dimer. If it bears two or more hydrogen atoms oligomerization may occur. Thus the phosphine, carbon compound or silane compound that is subjected to the catalytic reaction should be primary or secondary and, in general, the reaction proceeds more swiftly with primary compounds.

The substrate that is subjected to catalytic dehydrocoupling can be any hydrocarbon, organophosphorus, organosilicon, organotin or organoarsenic compound that bears one or two carbon atoms. In some cases, for instance with highly substituted compounds, static congestion creates potential for cleaving P-C bonds and prevents the coupling reaction, as for instance with 2,4,6-tri-t-butylphenylphosphine.

As indicated above, the mechanism of the catalytic reaction involves formation add then breaking of a bond between the zirconium atom and an atom of the monomer that is undergoing coupling. The affinity of that atom for zirconium is therefore a consideration; the catalytic reaction proceeds when the atom's affinity for zirconium is sufficiently great for formation of the zirconium-atom bond, but is not so great that the bond, once formed, will not break under the conditions of the reaction. Phosphorus, carbon and silicon usually satisfy these conditions. Nitrogen forms a strong bond with zirconium, so coupling of nitrogen compounds may not occur because the necessary breakage of the zirconium- nitrogen bonds will not occur.

When a phosphine or a silane are present in an organic solvent it might appear at first sight that there would be competition for reaction with the zirconium catalyst between the phosphine or silane, on the one hand, and primary or secondary carbon atoms of the solvent on the other hand. The affinities for zirconium of the phosphorus or silicon atoms differ sufficiently from the affinity of the carbon atom that the phosphorus or silicon will occupy all or almost all sites of the zirconium catalyst, so that there is little, if any, interference from solvents.

Phosphorus—phosphorus bonds have also been made by dehydrocoupling of bidentate phosphorus compounds for example ethylene diphosphine. $H_2PCH_2CH_2PH_2$. Examination of the product of this reaction by electron impact mass spectrometry revealed molecules of molecular weight about 1000, indicating that some oligomerization had occurred. Owing to its nature, electron impact mass spectrometry tends to understate the molecular weights of large molecules, as such molecules are readily broken into smaller fragments by the electron impact. Molecular fragments

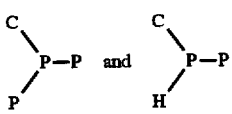

were also detected in the product by $^{31}$p NMR spectroscopy, indicating clearly formation of P—P bonds. Any phosphorus compound having terminal primary or secondary phosphine groups can be subjected to similar reaction, for example 1,2-, 1,3- or 1,4-phenylene-diphosphines and also the corresponding cyclohexyl-diphosphine compounds and other alkyl and cycloalkyl-diphosphine compounds. Similar remarks apply in respect of silicon, and silicon—silicon bonds have been detected from oligomerization of diphenyl silane in accordance with the invention. It is believed that tin compounds and arsenic compounds will also undergo similar reaction.

In Some instances the product of a dehydro-coupling reaction will be a cyclic product; for instance phenylphosphine forms pentaphenylcyclopentaphosphane. Some compounds, for instance the phenylene diphosphines, will be reluctant to cyclize and will form acyclic oligomers and polymers which may be straight or branched chained.

The novel compounds of formula I are useful for their catalytic activity. They catalyze dehydrocoupling of suitable hydrogen containing materials. Oligomers and polymers can be made by exploiting the anionic $Zr^{IV}$ species. If the substrate is a hydrogen-bearing phosphorus compound there can be obtained a phosphorus-containing oligomer or polymer. Such phosphorus polymers may find many uses. For example a phosphorus polymer may be used as a support for a catalyst and permit a catalytic reaction to be carried out heterogeneously, rather than homogeneously. This would permit adaptation of known homogeneous systems to heterogeneous catalyst, thereby permitting superior catalytic activity without the separation problems associated with homogeneous catalysis. Another use for a phosphorus polymer is recovery of precious metals from spent catalytic reactions by binding of the metals to the polymer. Yet another utility is as a precursor to a fire retardant. Phosphine oxide derivatives, in the form of small molecules, are known as effective fire retardants. By means of the catalyst of the invention phosphorus polymers can be obtained and some or all of the phosphorus atoms of the polymer oxidized to form a polymer containing many phosphine oxide moieties. The polymers are expected to be effective fire retardants, possibly more effective than the present non-polymeric phosphine oxide fire retardants.

The invention is further illustrated in the following Examples:

EXAMPLE 1

Preparation of potassium di(pentamethylcyclopentadienyl)zirconium trihydride tetrahydrofuran complex.

Dicyclopentadienyl zirconium dichloride (2 g, 1 equivalent), potassium hydride (0.75 g, 4 equivalents) and tetrahydrofuran (30 ml) were placed in a flask. These were stirred for 4–5 days. Bubbling occurred due to evolution of hydrogen. Thereafter excess potassium hydride was filtered off and then the THF was stripped off. Benzene (20 ml) was added to the residue, which was filtered again and then dried in vacuo. There was obtained an off-white or beige product, in about 60% yield.

In a variant of this procedure, after filtration to remove excess KH hexane was added to the THF solution and the mixture was cooled and allowed to stand at −30° C. There were formed pale yellow crystals, again in about 60% yield.

The reaction can be expressed by the following equation:

(Cp* is a recognized abbreviation for the pentaethylcyclopentadienyl moiety.) The structure of the product was confirmed by the following NMR data and elemental analysis $^1$H NMR (THF-d$_8$, 25° C.) 3.72 (br, 8H), 1.91 (s,30H), 1.70(d,2H, |J$_{H-H}$|=8.3 Hz), 1.52 (br,8H), −0.92 (t,1H, |J$_{H-H}$|= 8.3 Hz). $^{13}$C{$^1$H} NMR (THF-d$_8$, 25° C.) 110.6, 67.5, 26.1, 12.1.

Calculated for C$_{28}$H$_{49}$KO$_2$Zr , C,61·37; H,9·01.

Found: C, 61·18; H,8·97.

The $^1$H NMR spectrum of [Cp$_2$*ZrH$_3$][K(THF)$_2$] reveals a typical AX$_2$ pattern at 1.70(d) and −0.92(t) ppm with |J$_{H-H}$|=8.3 Hz. These resonances, attributed to three hydrides in two environments in a ratio of 1:2, show no temperature dependence between 50 and −50° C. while T$_1$ measurements for the two hydride resonances revealed similar relaxation times for these protons. X-ray crystallography confirmed this formulation, as the Cp*$_2$Zr and K(THF)$_2$ fragments exhibited typical metric parameters.

Similar reaction using excess potassium deuteride, KD, produced the corresponding trideuteride compound [Cp$_2$*ZrD$_3$][K(THF)$_2$].

EXAMPLE 2

The product of Example 1 was reacted with excess phenylphosphine (100 equiv) in dioxane at 120° C. and the primary phosphine was totally consumed after three days. The resulting phosphorus containing product exhibited a broad resonance at −5 ppm in the $^{31}$P NMR spectrum. The product, which crystallized from solution, was identified as P$_5$Ph$_5$ by high-resolution mass spectra, $^{31}$P NMR, preliminary X-ray crystallographic data and elemental analysis.

Under similar conditions cyclohexylphosphine and 2,4,6-trimethylphenylphosphine were converted into the compounds pentacyclohexylcyclopentaphosphane and penta-(2,4,6-trimethylphenyl)-cyclopentaphosphane, respectively. React ion with the 2,4,6-trimethylphenylphosphine proceeded more rapidly than with the cyclohexylphosphine, suggesting that steric congestion at the metal centre accelerates the reaction.

EXAMPLE 3

To monitor the stoichiometric reaction of the product of Example 1 with phenylphosphine, the product of Example 1 was reacted with 1 equivalent of phenylphosphine and NMR spectra were observed. 31P{$^1$H} and $^{31}$P NMR spectra revealed a weak singlet resonance at 465.8 ppm along with much stronger doublets at −49.2 and −89.1 ppm having |J$_{P-P}$| coupling of 335 Hz. The former resonance is similar In position to that observed for the phosphinidene hydride [Cp$_2$ZrH(P(C$_6$H$_2$-2,4,6-t-Bu$_3$))]$^-$; see Fermin et al., Organometallics, 1995, 14, 4247. This suggests formation of an analogous species, intermediate (b) given above. This species was short-lived, unstable and could not be isolated. On addition of a second equivalent of phenylphosphine it converted clearly to the intermediate (c). The $^{31}$P{$^1$H} NMR spectrum of intermediate (c) exhibited the two doublets at −49.2 and −89.1 ppm. The lower field half of this pattern also showed a |J$_{P-P}$| coupling of 41 Hz. Addition of hexanes to the THF solution afforded the isolation of this compound, identified as [Cp*$_2$Zr((PPh)$_2$)H][K(THF)$_4$]. In analogous reactions with 2 equivalents of cyclohexylphosphine (PCyH$_2$) and 2,4,6-trimethylphenylphosphine (P(C$_6$H$_2$-2,4,6-Me$_3$)H$_2$), the related compounds [Cp*$_2$Zr((PCy)$_2$)H][K(THF)$_4$] and [Cp*$_2$Zr((P(C$_6$H$_2$-2,4,6-Me$_3$))$_2$)H][K(THF)$_4$] were isolated. However, in the case of the catalytic reaction with 2,4,6-tri-t-butyl-phenylphosphine (P(C$_6$H$_2$-2,4,6-t-Bu$_3$)H$_2$), the extreme steric bulk resulted in the induction of P-C bond cleavage affording the substituent-free P complexes [Cp*$_2$Zr]$_2$(µ-P$_2$) and [Cp*$_2$Zr]$_2$(µ-P), previously reported by Fermin et al, J. Am. Chem. Soc., 1994, 116, 6033.

Reaction of intermediate (c) with an additional equivalent of PPhH$_2$ lead to the clean formation of a new species, intermediate (d), which exhibited a clean ABC pattern in the $^{31}$P{$^1$H} NMR spectrum with resonances also exhibiting a P-H coupling of 71 Hz. These data together with elemental analysis are consistent with the formulation of [Cp*$_2$Zr((PPh)$_3$)H][K(THF)$_4$]. The analogous products derived from PCyH$_2$ and P(C$_6$H$_2$-2,4,6-Me$_3$)H$_2$ were not observed at 25° C. while at elevated temperatures (60°–120° C.) only the polyphosphane products pentacyclohexyl-cyclopentaphosphane and penta-(2,4,6-trimethylphenyl)-cyclopentaphosphane were observed, i.e., the reactions proceeded directly to the final cyclopentaphosphane product. Similarly, addition of more PhPH$_2$ to intermediate (d) resulted in no further reaction at 25° C. while pentaphenyl-cyclopentaphosphane was formed at elevated temperatures (60°–120°).

EXAMPLE 4

The product of Example 1, [Cp*$_2$ZrH$_3$][K(THF)$_2$] was used to catalyze oligomerization of diphenylsilane, in accordance with the following procedure. Product of Example 1 (0.036 g) was placed in a 100 ml flask and there were added THF (2 ml), toluene (15 ml) and diphenylsilane (0.0605 ml). These were refluxed overnight at about 110° C., and then the solvent was stripped off. The residue was an oil, to which hexane was added. This was then filtered to remove impurities and the filtrate was collected, hexane was stripped off and the product dried in vacuo. The product was a yellow-orange oil of low solubility in benzene.

NMR analysis revealed a $^{29}$Si single peak at 18.20 and $^1$H showed phenyl peaks, but hydrides were difficult to find.

The data indicate formation of Si—Si bonds and polymerization.

EXAMPLE 5

The product of Example 1 was used to catalyze oligomerization of diphenylmethane. Product of Example 1 (0.028 g) was placed in e 100 ml flask and there were added THF (2 ml), toluene (15 ml) and diphenylmethane (0.043 ml). These were refluxed overnight at about 110° C. and then solvent was stripped off, The residue was washed with benzene and the mixture then filtered. Thereafter traces of benzene were stripped off and the product dried in vacuo.

The product was a white powder that was insoluble in benzene and in THF, hence, solution NMR analysis could not be used.

Electron impact mass spectrometry suggested formation of polymers with methylene sub-units, indicating that dehydrocoupling had taken place.

The ether layer was stripped off and the residue was redissolved In THF-d$_8$ and $^1$H NMR revealed the presence of trihydride; i.e., the [Cp*$_2$Zr$^{IV}$H$_3$]$^-$ ion.

EXAMPLE 6

The product of Example 1 was used to catalyze oligomerization of toluene. Product of Example 1 (0.026 g) was refluxed overnight in toluene (2 ml). Solvent was then stripped off and the product was extracted with benzene. The product was a white THF-insoluble material, indicating that dehydrocoupling and polymerization had occurred.

I claim:

1. A mononuclear Zr$^{IV}$ trihydride compound, monoalkyl dihydride compound or deuteride compound of the general formula I

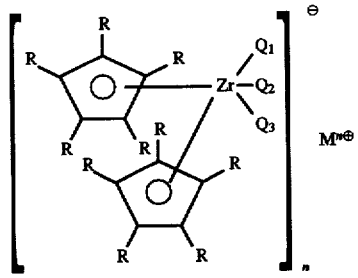

wherein:

each R is hydrogen or an electron-donating group, provided that at least two R groups attached to each cyclopentadienyl moiety are other than H;

M is a counter ion;

n is the valency of the counter ion;

Q$_1$ is selected from the group consisting of H, D, and CH$_3$; and

Q$_2$ and Q$_3$ are each selected from the group consisting of H and D, or a solvate thereof.

2. A compound according to claim 1 wherein at least three R groups attached to each cyclopentadienyl moiety are other than H and the compound of the general formula I is a trihydride.

3. A compound according to claim 1 wherein the counter ion is K$^+$, Na$^+$, Li$^+$, tetraalkylammonium$^+$, Ca$^{++}$ or Mg$^{++}$.

4. A compound according to claim 1 wherein all the R groups are alkyl groups having up to 8 carbon atoms.

5. A compound according to claim 1 wherein all the R groups are methyl or ethyl groups.

6. A compound according to claim 1 wherein the compound is In the form of an ether solvate.

7. A compound according to claim 1 which is the compound potassium di-(pentaethylcyclopentadienyl) zirconium trihydride.

8. A compound according to claim 7 wherein the compound is in the form of its solvate with tetrahydrofuran.

9. A process for preparing a mononuclear Zr$^{IV}$ trihydride compound, monoalkyl dihydride compound or deuteride compound according to claim 1, which process comprises reacting a zirconium compound of the general formula II,

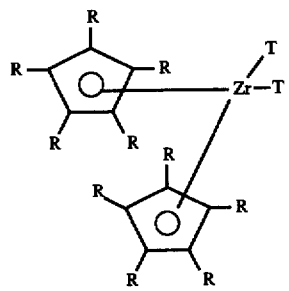

wherein R is as defined in claim 1 and T is a leaving group with an effective hydrogen transfer reagent or a corresponding deuterium transfer agent.

10. A process according to claim 9 wherein the hydrogen transfer reagent is used in stoichiometric excess.

11. A process according to claim 9 wherein the effective hydrogen transfer reagent is selected from the group consisting of potassium hydride, sodium hydride, lithium hydride, lithium aluminum hydride, sodium aluminum hydride, lithium aluminum hydrogen trialkoxide, sodium borohydride, calcium hydride, magnesium hydride and corresponding deuterium compounds.

12. A process according to claim 9 which is carried out In an ether as solvent.

13. A process according to claim 12 wherein the ether is selected from the group consisting of tetrahydrofuran dimethyl ether and dioxane.

14. A process according to claim 9 wherein di-pentaethylcyclopentadienyl)zirconium dichloride is reacted with potassium hydride.

* * * * *

UNITED STATES PATENT AND TRADEMARK OFFICE
CERTIFICATE OF CORRECTION

PATENT NO. : 5,726,335
DATED : March 10, 1998
INVENTOR(S) : Douglas W. Stephan

It is certified that error appears in the above-indentified patent and that said Letters Patent is hereby corrected as shown below:

Column 7, line 28, delete "Dicyclopentadienyl zirconium" and insert therefor --Di(pentamethylcyclopentadienyl) zirconium--.

Column 7, lines 46-47, delete "pentaethylcyclopentadienyl" and insert therefor --pentamethylcyclopentadienyl--.

Column 10, line 21, delete "di-(pentaethylcyclopentadienyl)" and insert therefor --di-(pentamethylcyclopentadienyl)--.

Column 10, lines 59-60, delete "di-pentaethylcyclopentadienyl)zirconium dichloride" and insert therefor --di- (pentamethylcyclopentadienyl) zirconium dichloride--.

Signed and Sealed this

Twenty-first Day of July, 1998

*Attest:*

BRUCE LEHMAN

*Attesting Officer*  Commissioner of Patents and Trademarks